(12) United States Patent
Caprarotta et al.

(10) Patent No.: US 9,357,826 B2
(45) Date of Patent: Jun. 7, 2016

(54) SOLID, COMPACT POWDER COSMETIC PRODUCT AND PROCESS FOR OBTAINING THE SAME

(75) Inventors: Grazia Anna Caprarotta, Verdello (IT); Marina Guanziroli, Chieve (IT)

(73) Assignee: COLOR COSMETICS S.R.L., Milan (IT)

( * ) Notice: Subject to any disclaimer, the term of this patent is extended or adjusted under 35 U.S.C. 154(b) by 541 days.

(21) Appl. No.: 12/892,206

(22) Filed: Sep. 28, 2010

(65) Prior Publication Data

US 2011/0293548 A1    Dec. 1, 2011

(30) Foreign Application Priority Data

Jun. 1, 2010    (IT) .............. MI2010A0993

(51) Int. Cl.
| | | |
|---|---|---|
| *A61K 8/73* | (2006.01) | |
| *A61K 8/02* | (2006.01) | |
| *A61Q 1/02* | (2006.01) | |
| *A61Q 1/08* | (2006.01) | |
| *A61Q 1/10* | (2006.01) | |
| *A61Q 1/12* | (2006.01) | |
| *A45D 40/16* | (2006.01) | |

(52) U.S. Cl.
CPC ............. *A45D 40/16* (2013.01); *A61K 8/022* (2013.01); *A61K 8/73* (2013.01); *A61Q 1/02* (2013.01); *A61Q 1/08* (2013.01); *A61Q 1/10* (2013.01); *A61Q 1/12* (2013.01)

(58) Field of Classification Search
CPC ........... A61K 8/73; A61K 8/733; A61Q 1/08; A61Q 1/02; A61Q 1/10; A61Q 1/12; A61Q 17/04; A61Q 13/00; A61Q 1/06; A61Q 1/04
See application file for complete search history.

(56) References Cited

U.S. PATENT DOCUMENTS

| | | | |
|---|---|---|---|
| 4,291,025 A | | 9/1981 | Pellico |
| 4,337,859 A | * | 7/1982 | Murphy et al. ............ 206/37 |
| 5,049,376 A | * | 9/1991 | Murphy et al. ............ 424/63 |
| 5,928,655 A | * | 7/1999 | Avalle ........................ 424/401 |
| 6,197,319 B1 | * | 3/2001 | Wang et al. ................ 424/401 |
| 6,660,253 B2 | * | 12/2003 | Maio et al. .................. 424/63 |
| 2006/0118197 A1 | * | 6/2006 | Avalle ............................ 141/1 |
| 2008/0044445 A1 | * | 2/2008 | Rubin ......................... 424/401 |
| 2009/0304609 A1 | * | 12/2009 | Allemand et al. ........... 424/59 |

FOREIGN PATENT DOCUMENTS

| | | |
|---|---|---|
| EP | 0803245 B1 | 9/2001 |
| EP | 1226811 | 7/2002 |
| JP | 62209011 A | 9/1987 |
| JP | 9175939 A | 7/1997 |
| JP | 2007186471 A | 7/2007 |
| WO | 0217875 A1 | 3/2002 |

OTHER PUBLICATIONS

Mintel, Mineral Air Pact Powder, Database GNPD (online), Mar. 1, 2009, XP002617375.
Mintel, D-Blush Blush Trios, Database GNPD (online), Dec. 1, 2008, XP002617376.
Dawydoff W., et al, Thermoreversible Gele auf Polysaccharidbasis, Nahrung, Food, VCH Verlagsgesellschaft, Weinheim, XX, Jan. 1, 1984, pp. 241-260, vol. 28, No. 3, XP007916772.
European Search Report (EP 10 18 0572) dated Jan. 19, 2011.
English language Abstracts for JP 2007186471; JP 62209011; and JP09175939.

\* cited by examiner

*Primary Examiner* — John Pak
*Assistant Examiner* — Nathan W Schlientz
(74) *Attorney, Agent, or Firm* — Fox Rothschild LLP

(57) ABSTRACT

The present invention provides a solid cosmetic product consisting of a substantially anhydrous, compact cosmetic powder comprising, as essential ingredients, one or more thermoreversible polysaccharides, one or more humectants, one or more emollients and a powder phase, and also optionally conventional cosmetic ingredients. The present invention further provides a process for obtaining such a solid, compact powder cosmetic product, which comprises the steps of making an aqueous paste using the essential ingredients and optionally conventional cosmetic ingredients, allowing the paste to solidify, and then subjecting the solidified paste to a heat treatment for removing water from the solidified paste.

9 Claims, 1 Drawing Sheet

SOLID, COMPACT POWDER COSMETIC PRODUCT AND PROCESS FOR OBTAINING THE SAME

CROSS-REFERENCE TO RELATED APPLICATIONS

This application claims priority to Italian Patent Application MI2010A000993, filed Jun. 1, 2010, the entirety of which is incorporated herein by reference.

FIELD OF THE INVENTION

The present invention relates to a solid, compact powder cosmetic product and a process for obtaining the same.

BACKGROUND

In EP-B-0803245 a solid, compact cosmetic gel containing water, thermoreversible polysaccharides, humectants and a powder phase is described and claimed.

This solid, compact cosmetic gel is a satisfactory cosmetic product but contains a high percentage of water, whereby it needs a sealed container or packaging to avoid volatile components from being lost.

Moreover, obtaining this solid cosmetic gel product with a relatively high volume is difficult, because it is prepared by heating and then poured into a special mould or container, in which cooling at room temperature causes a progressive shift in the gel internal bond (cross-linking) and the consequent solidification thereof without a clear solid-liquid transition.

The cosmetic product volume is thus determined from the mould or container volume, and in particular, when a product with a relief is required, this further limits the product volume.

DETAILED DESCRIPTION

Figure 1:
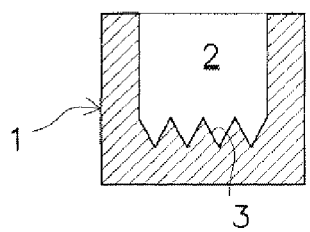
FIG. 1 shows a cross-sectional view of a container according to one embodiment.

It is the object of the present invention to provide a new solid cosmetic product which may have high volumes and possibly various types of reliefs.

In accordance with the present invention, such an object is achieved by a solid, compact powder cosmetic product which is characterized in that it consists of a substantially anhydrous cosmetic powder comprising, as essential ingredients, one or more thermoreversible polysaccharides, one or more humectants; one or more emollients, and a powder phase.

By "substantially anhydrous" is preferably meant that the water content in the final cosmetic product is 2% by weight or less.

The product contains one or more thermoreversible polysaccharides generally in an amount between 0.05 and 20% by weight of the final product, and preferably between 0.1 and 15% by weight of the final product.

Typical examples of suitable thermoreversible polysaccharides are carrageenan, agar, gellan gum, xanthan gum, biosaccharide Gum-1, alginic acid and alkaline metal or alkaline earth metal salts thereof. Further suitable examples may be found in the book "Biodegradable hydrogels for drug delivery", (1993), edited by K. Park et al., page 105, chapter 5.2, published by Technomic Publishing Co., Inc. Mixtures of various thermoreversible polysaccharides may also be used.

The product contains one or more humectants generally in an amount between 0.1 and 20% by weight of the final product, and preferably between 0.5 and 10% by weight of the final product.

Typical examples of suitable humectants are glycerine, sorbitol, mannitol, xilytol, glycols such as butylene glycol, pentylene glycol, hexylene glycol, dipropylene glycol, propylene glycol and polyethylene glycol. Others suitable examples may be found in C.T.F.A. Cosmetic Ingredient Handbook, First Edition, (1988). Mixtures of various humectants may also be used.

The product contains one or more emollients generally in an amount between 0.1 and 45% by weight of the final product, and preferably between 0.5 and 30% by weight of the final product.

Typical examples of suitable emollients are silicones, mineral oils, lanoline and derivatives thereof, vegetable oils, cetearyl alcohol esters, sorbitol esters, branch chain saturated hydrocarbons obtained by hydrogenation of the shark liver oil (squalane) or other natural oils, polyethylene glycol esters, potassium stearoyl, hydrolyzed rice proteins, esters with $C_{12\text{-}20}$ fatty acids of polyethylene glycol (8EO), cetearyl ethylhexanoate, polysorbate 80.

Further examples of suitable humectants may be found in the aforementioned C.T.F.A. Cosmetic Ingredient Handbook, First Edition, (1988). Mixtures of various emollients may also be used.

The product contains a powder phase generally in an amount between 0.1 and 90% by weight of the final product, and preferably between 5 and 80% by weight of the final product. Typical examples of a suitable powder phase are various common powder excipients used in make-up cosmetic products such as mica, kaolin, talc, fluorphlogopite, nylon 12, starch, zinc oxide, calcium sodium aluminium silicate, acrylate (co)polymers, polyethylene (co)polymers, silica, spherical silica, spherical silicones, pigments such as iron oxides, chromium oxides and hydroxides, ultramarine blue, ultramarine pink, manganese violet, titania, mica and titania or bismuth oxychloride-based pearlescent materials, carmine, organic colorant-based lacquers and others synthetic powder colorants. Mixtures of the various powder excipients and colorants may also be used.

In addition to the essential ingredients of the above-mentioned product, it may optionally contain conventional cosmetic ingredients such as preservatives, surfactants, emulsifiers, sunscreens, perfumes and flavourings, waxes, soaps, proteins, anti-caking agents, etc.

The solid, compact powder cosmetic product may be used as a make-up product such as foundation, blush, eye shadow, mascara, concealer, and so on.

The present invention overcomes the limitations of the previous solid, compact gel cosmetic product to a high extent and allows to obtain a solid, compact powder cosmetic product with a soft creaminess texture having extraordinary colour expressions and high volumes.

The product may be manufactured by means of conventional processes, e.g. by dry-mixing the various ingredients and then compacting the mixture under pressure in a specific mould or container, or by heating the various mixed ingredients to form a pourable paste or liquid followed by pouring the paste or liquid into a suitable mould or container and eventually let it solidify into the mould or container. However, these processes almost limit the possible desired volume of the product.

The present invention provides a preferred process for obtaining such a product in high volumes, thus particularly allowing the preparation thereof in particular shapes and patterns and geometries, with particular reliefs which are very difficult, if not impossible, to be obtained by means of conventional technologies.

The process according to the present invention substantially involves making an aqueous paste from the various ingredients of the product, which is then let solidify (jellify) into a suitable mould or container, and then the solidified or jellified paste is subjected to a heat treatment to remove the water from the paste itself.

The process according to the invention is exemplarily described with reference to the accompanying drawings, which show the various steps of the process.

First, a cosmetic product is prepared in a pasty form comprising thermoreversible polysaccharides, humectants, emollients, phase powders and containing also water or other solvents.

The solvent may entirely consist of water or proper mixtures of water and volatile or non-volatile organic solvents, such as for example aliphatic alcohols like ethanol, isopropanol, butanol, etc., in varying percentages.

The percentage of the above-indicated solvent or solvents in the paste may highly vary according to the viscosity degree required, and is preferably between 30% and 60%.

A container which has an internal cavity with a shape complementary to the one desired for the final cosmetic product is also arranged. A container example is shown in FIG. 1, where the container is indicated as a whole by reference numeral 1, its internal cavity is indicated by 2, and the shaped bottom of said cavity is indicated by 3.

A container made of metal, silicone or other plastic material, e.g. polyurethane resin, polycarbonate, methacrylate and many others, may be used.

The use of these materials is justified in that the plastics may be moulded both by injection into a mould and by polymerization in a bi-component liquid form around a metal template, and in both cases, the shapes may be highly various and very well defined, with very marked, sharp reliefs even with very acute angles.

The cosmetic paste product is then heated at an average temperature of 90° C., or in any case between 70° C. and 90° C., to make it so fluid to be pourable into the container.

Figure 2:
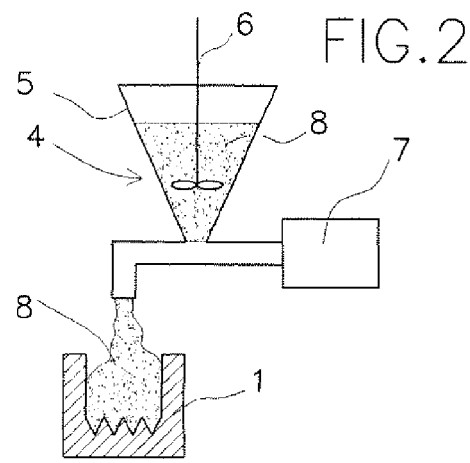
FIG. 2 shows a cross-sectional view of a volumetric piston doser according another embodiment and illustrates a dosing method according to one embodiment.

The dosing step may be carried out by a volumetric piston doser, as shown in FIG. 2, where reference numeral 4 indicates the doser as a whole, 5 indicates a loading hopper, 6 indicates a stirrer, 7 indicates a piston doser, and 8 in the end indicates the fluid paste being dosed.

Alternatively, a common dosage system with a gear pump or other may also be employed.

Once the product has been heat-dosed into container 1, it is allowed to cool so as to conform to the inner shape of the mould. The cosmetic product cools down and jellifies very quickly until adopting a semisolid consistence.

The jellified cosmetic product, indicated by 8', may then be quickly drawn from the mould, if this is made of flexible materials, such as silicone, and then allowed to dry without the container, or allowed to dry directly within the mould itself, if this is made of rigid plastic materials, for example polycarbonate, polyurethane resin, etc.

The heat treatment is usually carried out at temperatures between 20° C. and 90° C., preferably between 35° C. and 80° C. This heat treatment may be carried out by any suitable heating method, such as for example in an air-recycle, humidity-controlled vented oven, a micro-wave oven or other. The heating should be performed over a sufficient period to make the product substantially anhydrous and this depends on the amount of water in the paste and on the temperature at which the heating is carried out.

In the case of humidity-controlled, forced ventilation ovens, the heating may last 12-24 hrs.

Figure 3:
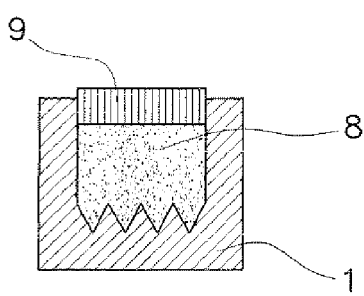
FIG. 3 shows a cross-sectional view of cosmetic product within the container of FIG. 1.

Once the cosmetic product has been dried, it should be stuck within the final container for sale, and for this purpose, the product may directly be placed within the final container or a shaped strap 9 may be placed on the liquid paste 8, immediately after the dosing step, in contact with the upper surface of the cosmetic product, as shown in FIG. 3.

Thereby, by adhering to the product during the jellifying and cooking steps, strap 9 will form a single body with the product itself.

The thickness of such a strap may range between 3 mm and more, and its shaping will correspond to that of the base of the intended shape.

Without distinctions, the material employed for strap 9 may be a natural product, such as baked clay, porcelain, chalk, paper or cellulose agglomerates, etc., but also compacted synthetic materials, e.g. plastics such as polycarbonate, polyethylene, Plexiglas, etc. or expanded materials, such as expanded polyurethane, expanded polyethylene, expanded phenolic resins, etc.

The strap may be employed as such or coated with a proper adhesive, to enhance the gripping abilities thereof.

Figure 4:
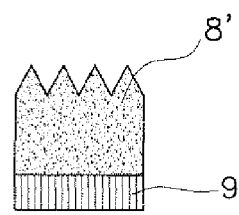
FIG. 4 shows a cross-sectional view of cosmetic product after removal from the container of FIG. 1 with a strap serving as a support for the cosmetic product.

As already mentioned, the drying operation may be carried out upon extraction of the jellified cosmetic product from container 1. In such a case, the product-strap assembly may also be overturned so that strap 9 serves the function as a support for the cosmetic product, as shown in FIG. 4.

Once the cosmetic product has been dried, in association with its corresponding strap, it is ready to be inserted and stuck into the final container intended to sale.

It is another advantage obtained by this technique to provide plug powder cosmetic products. In the known art, the final product consisting of different plugs of product is generally obtained through various steps: every single plug is pre-compacted into a single mould, then drawn from said mould and placed in the final cup where, once all the plugs have been placed, the final compacting step is carried out, and the final product is obtained. The limit of this technique is the large amount of steps to be carried out, the high cost for manufacturing several moulds, the shape limitations due to the metal cups, and the long manufacturing times.

Figure 5:
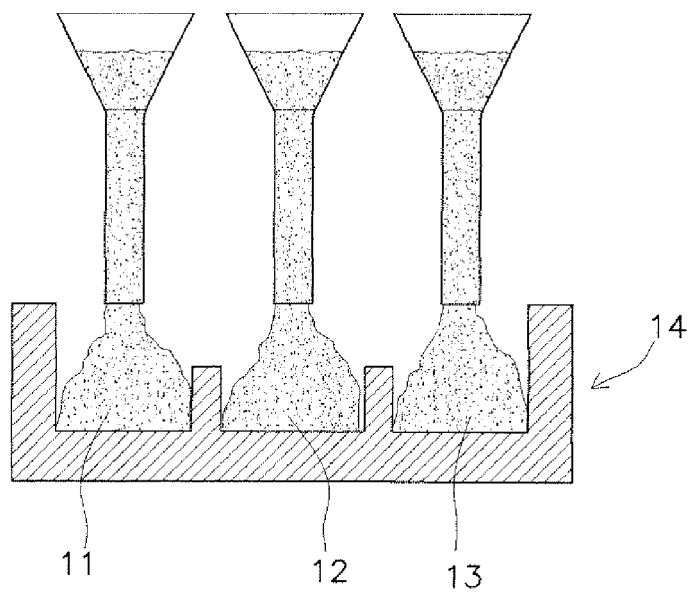
FIG. 5 shows a cross-sectional view of a mold according to yet another embodiment and illustrates a method of simultaneously dosing various products according to one embodiment.

By means of the new method according to the present invention plug powder cosmetic products may be obtained in only two steps, that is by simultaneously dosing the various products of the single plugs 11, 12, 13 into a single mould 14 (FIG. 5), and once the mould has been filled, the water or solvents may be drained off by means of a heat treatment, as mentioned above. The advantages of this new technique are the decrease in manufacturing costs and the possibility of obtaining whichever shapes and volumes.

Furthermore, the method according to the invention suppresses employing clothes as a gap between the cosmetic product and the mould, and thus also suppresses the weft and haze left by the clothes on the surface of the compacted cosmetic product.

Another important aspect is the consistency of the obtained product, i.e. very compact and soft, more impact-resistant than other powder products. This is just due to the presence of the compact solid gel formed from the dried paste, which confers a porous and aerated texture to the product.

The following is an example not exhaustive and not limiting of the composition of the product according to the invention, prepared according to the above-described preferred process of the invention.

Example

| Ingredients | % WT/WT | |
|---|---|---|
| MICA | 27.521 | A |
| TITANIA CI 7789 | 16.813 | |
| ALUMINIUM CALCIUM SODIUM SILICATE | 16.627 | |
| IRON OXIDES CI 77491 | 9.099 | |
| CETEARYL ETHYLHEXSANOATE | 6.873 | |
| IRON OXIDES CI 77499 | 5.010 | |
| C12-20 ACID PEGs-8 ESTER | 4.205 | |
| RAFFINOSE ISOSTEARATE | 4.124 | |
| HDI/TRIMETHYLOL HEXILLATONE XPOLYMER | 3.276 | |
| GLYCERINE | 2.491 | |
| FERRIC FERROCYANIDE CI 77510 | 0.795 | |
| GLYCERINE | 0.500 | B |
| GELLAN GUM | 0.180 | |
| CAPRYLYL GLYCOL | 0.500 | C |
| POTASSIUM CETYL PHOSPHATE | 0.438 | |
| POLISORBATE 20 | 0.404 | |
| 1,2-HEXANEDIOL | 0.250 | |
| TIN OXIDE | 0.087 | |
| SILICA | 0.067 | |
| SYNTETIC FLUORPHLOGOPITE | 0.040 | |
| STEAROYL POTASSIUM | | |
| HYDROLYZED RICE PROTEIN | 0.200 | |
| SQUALANE | 0.500 | |
| Total | 100.000 | |

This product was prepared as follows.

The ingredients mentioned above as A were mixed to form a powder phase (a). The ingredients mentioned above as B were then mixed with water to form a phase (b). The ingredients mentioned above as C were then mixed to form a phase (c). Phase (b) was then put into a turbo-emulsifier and heated at 75° C., and phase (c) was then added under stirring and thus the mixture was homogenized. The resulting emulsion was lastly cooled down at 25° C.

Phase (a) was then mixed with the emulsion, together with ethanol to obtain a paste. Water and calcium chloride as a catalyst were added to this paste to obtain a gel, and the resulting liquid paste was then poured into a mould, where it was then heated at 80° C. and kept at this temperature for more than 6 hrs. Finally, a compact solid powder was obtained with a very creamy texture and high volume.

The invention claimed is:

1. A process for preparing a solid compact powder cosmetic product comprising, as essential ingredients:
   one or more thermoreversible polysaccharides;
   one or more humectants;
   one or more emollients; and
   a powder phase,
   said product comprising 2% or less water, the % being by weight of the product,
   the process comprising the steps of:
   a) providing an aqueous paste with said essential ingredients and optionally with conventional cosmetic ingredients;
   b) heating said aqueous paste to render it pourable;
   c) pouring said aqueous paste into a mould or container;
   d) gelling said paste in said mould or container to produce a gel paste; and
   e) subsequently subjecting the gel paste to a heat treatment to remove water from the gel paste to obtain a final solid compact cosmetic product comprising 2% or less water, the % being by weight of the product.

2. The process of claim 1, wherein said product is anhydrous.

3. The process of claim 1, wherein said product comprises:
   one or more thermoreversible polysaccharides in an amount of from 0.05 to 20% by weight of the final product;
   one or more humectants in an amount of from 0.1 to 20% by weight of the final product;
   one or more emollients in an amount of from 0.1 to 45% by weight of the final product; and
   a powder phase in an amount of from 0.1 to 90% by weight of the final product.

4. The process of claim 3, wherein said product comprises:
   one or more thermoreversible polysaccharides in an amount of from 0.1 to 15% by weight of the final product;
   one or more humectants in an amount of from 0.5 to 10% by weight of the final product;
   one or more emollients in an amount of from 0.5 to 30% by weight of the final product; and
   a powder phase in an amount of from 5 to 80% by weight of the final product.

5. The process of claim 1, wherein the product further comprises conventional cosmetic ingredients.

6. The process of claim 1, wherein the heat treatment is carried-out at a temperature between 20° C. and 90° C.

7. The process of claim 6, wherein the heat treatment is carried out at a temperature between 30° C. and 80° C.

8. The process of claim 1, further comprising pressing one or more reliefs on the surface of the solidified paste in the mould.

9. The process of claim 1, wherein the product is formed into multicolored plugs.

* * * * *